(12) United States Patent
Dobbins et al.

(10) Patent No.: US 6,806,356 B2
(45) Date of Patent: Oct. 19, 2004

(54) PROCESS FOR RECOVERING SECOISOLARICIRESINOL DIGLYCOSIDE FROM DE-FATTED FLAXSEED

(75) Inventors: Thomas A. Dobbins, Howard, OH (US); David B. Wiley, Warsaw, OH (US)

(73) Assignee: Wiley Organics, Inc., Coshocton, OH (US)

( * ) Notice: Subject to any disclaimer, the term of this patent is extended or adjusted under 35 U.S.C. 154(b) by 0 days.

(21) Appl. No.: 10/405,869

(22) Filed: Apr. 2, 2003

(65) Prior Publication Data

US 2003/0216553 A1 Nov. 20, 2003

Related U.S. Application Data

(60) Provisional application No. 60/369,270, filed on Apr. 2, 2002, and provisional application No. 60/420,417, filed on Oct. 22, 2002.

(51) Int. Cl.[7] .......................... C07G 1/00; C08L 97/00
(52) U.S. Cl. ........................................ 530/500; 530/507
(58) Field of Search ................................. 530/500, 507

(56) References Cited

U.S. PATENT DOCUMENTS

| | | |
|---|---|---|
| 5,705,618 A | 1/1998 | Westcott et al. |
| 5,846,944 A | 12/1998 | Prasad |
| 5,925,401 A | 7/1999 | Kankaanpää-Anttila et al. |
| 5,928,696 A | 7/1999 | Best et al. |
| 6,264,853 B1 * | 7/2001 | Westcott et al. ............... 252/1 |
| 6,355,816 B1 | 3/2002 | Dobbins |
| 2001/0003781 A1 | 6/2001 | Dobbins et al. |

FOREIGN PATENT DOCUMENTS

WO 99/34810 7/1999

OTHER PUBLICATIONS

Rickard, Sharon E. et al "Dose-dependent production of mammalian lignans in rats and in vitro from the purified precursor secoisolariciresinol diglycoside in flaxseed", Aug., 1966, The Journal of Nutrition, vol. 126, Iss. 8: pp 2012–2020.*

P.A. Ireland et al., "Saponins Content of Soya and Some Commerical Soya Products by Means of High–performance Liquid Chromatography of the Sapogenins," *J. Sci. Food Agric.*, pp. 694–698 (1986).

K. Hostettmann et al., "Saponins, Chemistry and Pharmacology of Natural Products," *Cambridge University Press*, pp. 142–145.

* cited by examiner

Primary Examiner—Nathan M. Nutter
(74) Attorney, Agent, or Firm—Thompson Hine LLP

(57) ABSTRACT

A process for extracting secoisolariciresinol diglycoside (SDG) from de-fatted flaxseed is described. The process comprises contacting defatted flaxseed with an extraction solvent of acetone and water, extracting the de-fatted flaxseed with the extraction solvent to extract SDG-containing compounds, removal of solvents, followed by alkaline hydrolysis of the extract to liberate free SDG or its salts.

18 Claims, No Drawings

PROCESS FOR RECOVERING SECOISOLARICIRESINOL DIGLYCOSIDE FROM DE-FATTED FLAXSEED

CROSS REFERENCE TO RELATED APPLICATIONS

This application claims priority from U.S. Provisional Application Ser. No. 60/369,270, filed Apr. 2, 2002 and U.S. Provisional Application Ser. No. 60/420,417, filed Oct. 22, 2002.

BACKGROUND OF THE INVENTION

This invention relates to an improved process for the extraction, isolation, and purification of secoisolariciresinol diglycoside (SDG) from de-fatted flaxseed.

Flaxseed is presently grown for its oil content, used primarily as an industrial oil. The scientific literature contains an abundance of reports on the chemistry and physical properties of various components derived from de-fatted flaxseed. Recently, considerable interest has been demonstrated in a class of minor compounds contained in flaxseed collectively referred to as lignans.

Lignans are generally dimers containing a dibenzylbutane skeleton. When part of the human diet, these compounds are believed to be converted into the mammalian lignans known as enterolactone and enterodiol. (Thompson et al. "Mammalian Lignan Production from Various Goods", *Nutr. Cancer* 16:43–52, (1991).) The principal lignan found in flaxseed is secoisolariciresinol diglucoside, referred to hereinafter as SDG.

Flaxseed typically contains 40% by weight fat ("linseed oil"). De-fatted (hexane-extracted) flax seed contains a residue of about 2% by wt. fat, with the remainder comprising: 46% by wt. fiber (both water-soluble fiber or "mucilage," acidic heterogeneous polysaccharides that contain galacturonic acid, galactose, rhamnose, and xylose, comprising 30–40% of the total fiber present, and water-insoluble fiber, which comprises 60–70% of the total fiber present); 10% total other carbohydrates, including lignans; 35% by wt. protein; 6–7% ash.

Appreciable amounts of free SDG do not occur in the de-fatted flaxseed. This compound must be liberated by alkaline hydrolysis of various ester-linked polymers. According to the literature, the available SDG in de-fatted flaxseed ranges from 0.9% to 3.0% by wt. (Thompson et al. "Mammalian Lignan Production from Various Goods", *Nutr. Cancer* 16:43–52, (1991).)

There is considerable published evidence indicating that lignans as a class of compounds exhibit a broad spectrum of biological activities, including anti-tumor, anti-mitotic, anti-oxidant, anti-viral, weak estrogenic and anti-estrogenic activities. Studies conducted by the chemotherapy program of the National Cancer Institute indicate that some lignans prevent the growth of tumors. (Thompson et al, "Anticarcinogenic Effect of a Mammalian Lignan Precursor from Flaxseed", *Proc. 55th Flax Institute of U.S.A.*, Fargo, N. Dak., 46–50 (1194).)

Even though there would appear to be very significant commercial uses for lignans like SDG in food supplements, nutraceuticals, and medicines, SDG has remained a laboratory curiosity, principally because it is available in only very limited quantities. To date, only one commercial process has been developed for the extraction and isolation of SDG from flaxseed. Disclosed herein is an improved process for extracting and isolating SDG from de-fatted flaxseed in order to make the compound available less expensively not only in large quantities, but at a purity suitable for use as a nutritional supplement or nutraceutical.

In 1956 Bakke and Klosterman described a laboratory process for extracting SDG from defatted flaxseed using equal parts of 95% ethanol and 1,4-dioxane. (Bakke and Klosterman, "A New Diglucoside from Flaxseed", *Proceedings of the N. Dakota Academy of Science* 10:18–22 (1956).)

Prior publications also refer to methanolysis of complexed SDG (i.e. the ester-linked polymers) and to the use of a sodium or barium methoxide for methanolysis to release non-complexed SDG.

U.S. Pat. No. 5,705,618 issued to Wescott et al, entitled "Process for Extracting Lignans from Flaxseed," teaches a process for extracting and isolating SDG from de-fatted flaxseed that employs the following sequence of operations:

1.) De-fatted flaxseed meal is contacted with an "aliphatic alcohol solvent" (i.e. mixtures of methanol, ethanol, isopropanol, or butanol with water) to extract the SDG-containing lignan precursor.
2.) Residual solids are separated from the lignan-rich alcohol-water solvent and the lignan-containing extract is then concentrated by removing solvent by distillation until a syrup is obtained.
3.) SDG is liberated from its lignan precursor compounds by hydrolysis of the syrup at an elevated pH.
4.) The hydrolyzed aqueous concentrate is subjected to a liquid/liquid partition to further enrich the SDG. The preferred embodiment calls for the use of ethyl acetate to remove impurities that include the methyl esters of cinnamic acids and other cinnamic acid derivatives. Alternatively, the SDG-containing aqueous phase may be subjected to contact with an anion exchange resin to remove impurities.
5.) The aqueous hydrolysate is subjected to chromatographic separation using reverse-phase high-pressure liquid chromatography ("HPLC") to isolate SDG.

U.S. Pat. No. 5,705,618 teaches the use of mixtures of aliphatic alcohols and water as the extraction solvent, with preference for alcohol-to-water ratios ranging from 1.85:1 to 3:1.

SUMMARY OF THE INVENTION

The present invention employs mixtures of acetone and water instead of aliphatic alcohols and water as the extraction solvent to extract SDG from de-fatted flaxseed.

In accordance with one aspect of the invention, a process for extracting secoisolariciresinol diglycoside (SDG) from de-fatted flaxseed is described. The process comprises contacting defatted flaxseed with an extraction solvent of acetone and water, extracting the de-fatted flaxseed with the extraction solvent to extract SDG-containing compounds, removal of solvents, followed by alkaline hydrolysis of the extract to liberate free SDG or its salts.

In accordance with another aspect of the present invention, a process for preparing a secoisolariciresinol diglycoside (SDG) concentrate from de-fatted flaxseed is disclosed. The process involves extracting defatted flaxseed with an extraction solvent of acetone and water to obtain an SDG-containing extract, separating residual solids from the SDG-containing extract, removing acetone to provide an acetone stripped extract, lowering the pH of the acetone stripped extract to precipitate SDG, separating precipitated SDG from the acetone stripped extract, subjecting the precipitated SDG in an aqueous slurry to hydrolysis to liberate free SDG and recovering the free SDG from the aqueous slurry.

In accordance with particular aspects of the invention, the precipitated SDG in the extract solution is subjected to hydrolysis to free the SDG from polymeric lignan precursor compounds. In accordance with particularly useful embodiments of the present invention, calcium hydroxide is used to liberate free SDG. The resulting SDG concentrates obtained using calcium hydroxide are non-hygroscopic and easily separated from insoluble calcium salts to provide a product of relatively high purity.

DETAILED DESCRIPTION OF THE INVENTION

The present invention relates to an improved process for the extraction, isolation, and purification of secoisolariciresinol diglycoside (SDG) from de-fatted flaxseed. The process of the invention utilizes an extraction solvent comprising acetone and water to extract SDG from de-fatted flaxseed. The acetone-water solvent increases efficiency and selectivity of the extraction. Furthermore, the acetone can be easily removed after extraction and reused, thereby minimizing solvent usage.

The proportion of acetone to water will typically range from about 35% acetone/65% water by weight to about 65% acetone/35% water by weight. In accordance with one embodiment, the solvent contains about 45% acetone/55% water by weight.

The acetone-water solvent will typically be employed in a ratio of about 6 or more parts by weight solvent mixture to about 1 part by weight de-fatted flaxseed. Preferably, the solvent to feedstock ratio is in the range of about 12:1 to 16:1.

Although the extraction may be performed over a wide range of temperatures for various periods of time, in accordance with one embodiment, it is performed at acetone reflux for about 90 minutes with vigorous agitation.

The mixture is then filtered or centrifuged to remove the undissolved solids. Filtration or centrifugation is preferably performed at elevated temperatures, e.g., exceeding about 50° C., to retain the SDG in solution.

About 18 to 20% of the mass of the feedstock may dissolve in the solvent. More than about 85% of the SDG-containing lignan precursor from the feedstock is generally contained in the extract from a single extraction.

Acetone is removed by distillation from the filtrate or centrifugate and recovered for re-use.

The acetone-water extraction solvent of the present invention enjoys several important advantages over the alcohol-water solvents of U.S. Pat. No. 5,705,618, notably:

1.) Improved efficiency of extraction per unit weight of solvent employed.
2.) Improved selectivity of extraction.
3.) Greater ease of solvent recovery. Unlike ethanol, isopropanol, and butanol, acetone does not azeotrope (i.e. form a constant boiling mixture) with water, making it easier to separate from the product-containing extract and recover for reuse.
4.) Acetone is far less toxic than methanol and emissions of acetone are not regulated under the Clean Air Act like those of methanol, ethanol, isopropanol, and butanol.

In accordance with certain embodiments of the present invention, calcium hydroxide may be used to liberate free SDG from the polymeric lignan precursor compounds that fall out of solution when acetone is removed from the de-fatted flaxseed extract by distillation. Sufficient calcium hydroxide is added to the aqueous slurry to achieve a pH of 10 to 13 (preferably 11.8 to 12.5), whereupon the resulting alkaline mixture is heated to approximately 50 to 100° C. (preferably to about 70 to 90° C.) with agitation for a period of 30 minutes or more (preferably for a period of one to four hours) to effect the hydrolysis of the SDG-containing polymeric lignan precursor compounds.

After the alkaline hydrolysis is complete, the pH is lowered to a value of from about 6.5 to 8.5 (preferably to about 7.5) by adding phosphoric acid. Upon cooling, insoluble calcium phosphates (principally dibasic calcium phosphate or calcium monohydrogen phosphate; $CaHPO_4$) fall out of solution and can be removed by filtration or centrifugation. The SDG remains in the filtrate or centrate.

One advantage of employing calcium hydroxide over alkalies of the Group I metals (i.e. sodium and potassium hydroxides or carbonates) is that dibasic calcium phosphate is only very sparingly soluble in water and can be readily separated from the post-hydrolysis SDG-containing aqueous solution by filtration or centrifugation. If sodium or potassium hydroxides or carbonates are employed, the sodium and potassium salts of phosphoric acid and other mineral acids (i.e., sulfuric acid, hydrochloric acid, etc . . . ) are highly soluble in the post-hydrolysis SDG-containing aqueous solution. Hence these salts cannot be readily separated from the SDG, resulting in a product of lower purity. Although these compounds provide lower purity, their use is still within the scope of the present invention which is not limited to any particular method for subjecting the SDG precipitate to hydrolysis.

A second advantage of employing calcium hydroxide is that the resulting SDG concentrates are not hygroscopic, unlike SDG concentrates prepared with sodium or potassium hydroxides or carbonates.

The SDG can be recovered by removing water by lyophilization, spray drying, vacuum drying, or other evaporative means to provide an SDG concentrate in a yield of at least about 70%, preferably at least about 85% and in accordance with certain embodiments as high as about 90% or greater.

The invention is illustrated by the following non-limiting examples:

EXAMPLE 1

3,510 grams of acetone was added to 4,290 grams of water to form a solvent consisting of 45% by weight acetone, 55% by weight water. This solvent was charged to a 12-liter three-necked flask equipped with a heating mantle, paddle stirrer, reflux condenser, and thermal well. 600 grams of de-fatted flaxseed (1.29% by weight SDG contained) was added; the resulting mixture was then heated to acetone reflux while maintaining vigorous agitation.

After 90 minutes at reflux, the mixture was allowed to cool to 50° C., then it was filtered through Whatman #4 paper on a Buechner funnel to remove insoluble solids. The filter cake was dried in vacuo at 80 degrees C. and weighed to give a mass of 486 grams; 114 grams (19%) of the de-fatted flaxseed dissolved in the solvent.

The filtrate was charged to a still and acetone was removed by fractional distillation and recovered for re-use.

As the acetone was removed, dark brown, cohesive, asphalt-like semi-solids ("tars") fell out of solution. The pH of the aqueous, acetone-stripped extract was 5.7.

Once the acetone was removed, the tars were allowed to settle to the bottom of the vessel. Settling was extremely rapid, and the tars occupied less than 2% of the volume of aqueous, acetone-stripped extract. The turbid supernatant aqueous extract was decanted at a temperature of 85 degrees C. to a separate vessel. (The tars, which contain approximately 15% of the extracted lignans, rapidly blind filters, rendering recovery of the product contained in the aqueous, acetone-stripped extract far more difficult. Consequently, the product contained in the tars may be recovered separately and recombined with the product from the decanted aqueous acetone-stripped extract in a subsequent step.)

The decanted aqueous acetone-stripped extract was cooled to a temperature of 30 degrees C. The pH was lowered to a target value of 3.0 about by adding 9 grams of dilute (10% by wt.) hydrochloric acid in order to precipitate any lignans remaining in solution. Upon acidification, additional very finely divided tan or buff-colored product will fall out of solution.

The acidified solution is cooled to 10 degrees C. 2.5 grams of Celite filter agent (acid-washed diatomaceous earth containing >95% by weight silicon dioxide) were added, then the extract was filtered through Whatman #4 filter paper on a Buechner funnel. Filtration was rapid with no blinding, yielding a transparent, non-turbid, pale yellow filtrate that will not contain appreciable amounts of product.

The filter cake was slurried in 100 ml of water and digested at an elevated pH in order to liberate free SDG from its precursor polymeric complexes. 6 grams of a 50% by wt. aqueous NaOH solution were added to the slurry, elevating the pH to 11.8. The mixture is agitated gently while maintaining a temperature of 35 to 40 degrees C. for 90 minutes. The color of the solution darkened markedly to a dark brown color.

The "tars" were digested at a pH of 11.8 in an identical fashion, then the resulting solution was combined with the solution from the decanted fraction.

The pH of the combined alkaline hydrolysis solutions was then lowered to a target value of 3.5 by the dropwise addition of dilute hydrochloric acid. A voluminous precipitate formed immediately and was removed by filtration through Whatman #4 paper on a Buechner funnel. Due to the presence of the Celite filter agent, filtration was very rapid, with no blinding. The solids were washed with a modest quantity of acidified (pH=3.5) water. The mass of this filter cake (which does not contain an appreciable quantity of lignans) was 9.7 grams (7.2 grams of waste product and 2.5 grams of Celite).

The entrained waste product was removed by slurrying the filter cake with a dilute aqueous solution of sodium hydroxide at a pH of 12, filtering through Whatman #4 paper, and washing the filter cake, which consists of Celite filter agent that can be re-used rather than discarded.

The filtrate was adjusted to a pH of 5.7 to 5.8 by the dropwise addition of an aqueous solution of sodium hydroxide, then lyophilized to give 19.3 grams of a light-colored, fluffy hygroscopic solid containing 31% by wt. SDG, corresponding to a recovery of 90% of the SDG that was initially extracted from the 600 grams of de-fatted flaxseed.

EXAMPLE 2

4,500 grams of acetone was added to 5,550 grams of water to form a solvent consisting of 45% by weight acetone, 55% by weight water. This solvent was charged to a 22-liter three-necked flask equipped with a heating mantle, paddle stirrer, reflux condenser, and thermal well. 1,000 grams of de-fatted flaxseed (1.29% by weight SDG contained) was added; the resulting mixture was then heated to acetone reflux while maintaining vigorous agitation.

After 90 minutes at reflux, the mixture was allowed to cool to 50° C. and 21 grams of Cellulose filter aid added. The acetone was then removed by fractional distillation and recovered for re-use. As the acetone was removed, dark brown, cohesive, asphalt-like semi-solids ("tars") fell out of solution. The pH of the aqueous, acetone-stripped extract was 5.7.

Once the acetone was removed, the slurry was cooled to <30° C. and the pH was lowered to 3.0 by adding 14 grams of concentrated hydrochloric acid. Upon acidification, additional very finely divided tan or buff-colored solids fell out of solution.

Agitation was ceased and the contents of the flask were allowed to settle for a period of 4 hours while cooling to 20° C. The clear, pale yellow supernatant liquid was decanted and disposed as waste. The remaining liquid and solids were combined and centrifuged; the centrate was discarded. The solids were re-slurried with 600 milliliters deionized water and centrifuged, once again discarding the centrate. (The wash and centrifugation removes saccharides, which would lower the purity of the final product.)

The solids were slurried with 200 milliliters of deionized water and 5 grams of calcium hydroxide were added to achieve a pH of 11.8. The slurry was then heated to 70° C. and maintained at 69–72° C. for one hour. The pH was re-checked after a period of 20 minutes and an additional 0.8 grams of calcium hydroxide were added to maintain the target pH of 11.8.

The slurry was then filtered at 70° C. through Whatman #4 paper on a Buechner funnel to remove insoluble solids and any unreacted calcium hydroxide. The paper was pre-coated with Celite 545 filter aid (diatomaceous earth) to enhance filtration. Filtration was rapid with no blinding. The filter cake was washed with 50 milliliters deionized water.

The filtrate and wash were combined and heated to a temperature of 60–70° C., the pH adjusted to 7.5 with 5.5 grams of concentrated phosphoric acid, then cooled to 20–25° C. Calcium phosphate and other light-colored solids precipitated were removed by filtration thru Whatman #4 filter paper on a Buechner funnel pre-coated with Celite filter aid. The filter cake was then washed with 50 milliliters of deionized water.

The filtrate and wash were combined and lyopholized to give 20.5 grams of a tan-colored, fluffy solid containing 43.4% by wt. SDG, corresponding to a recovery of 90% of the SDG that was initially extracted from the 1,000 grams of de-fatted flaxseed. This material is not hygroscopic.

What is claimed is:

1. A process for extracting secoisolariciresinol diglycoside (SDG) from de-fatted flaxseed comprising:
    (a) contacting defatted flaxseed with an extraction solvent comprising acetone and water at proportions ranging from about 35% acetone/65% water to about 65% acetone/35% water;
    (b) extracting said de-fatter flaxseed with the extraction solvent to extract SDG into said extraction solvent; and
    (c) separating residual solids from the SDG-containing extract.

2. The process of claim 1 wherein the weight the of extraction solvent to the weight of the de-fatted flaxseed is at least about 6:1.

3. The process of claim 2 wherein the weight the of extraction solvent to the weight of the de-fatted flaxseed is in the range of about 12:1 to about 16:1.

4. The process of claim 1 further comprising:
    (d) removing acetone from said extract;
    (e) subjecting said SDG-containing extract to hydrolysis to liberate free SDG; and
    (f) recovering said free SDG.

5. The process of claim 1 wherein the step of extracting the de-fatted flaxseed is carried out at an elevated temperature.

6. The process of claim 5 wherein the step of extracting the de-fatted flaxseed is carried out at acetone reflux.

7. The process of claim 1 wherein the step of separating the residual solids from the SDG-containing extract is carried out at an elevated temperature to retain the SDG in solution.

8. The process of claim 1 further comprising:
   (d) removing acetone from said extract;
   (e) lowering the pH of said extract to precipitate SDG;
   (f) subjecting said precipitated SDG to hydrolysis to liberate free SDG; and
   (g) recovering said free SDG.

9. The process of claim 8 wherein step (f) comprises alkaline hydrolysis.

10. The process of claim 9 wherein said alkaline hydrolysis comprises adding calcium hydroxide to an aqueous slurry containing said precipitated SDG to provide an alkaline mixture having a pH of about 10 to about 13.

11. The process of claim 10 wherein said alkaline hydrolysis is carried out at an elevated temperature.

12. The process of claim 8 wherein said step of recovering free SDG comprises removing water by lyophilization, spray drying, vacuum drying, or other evaporative means.

13. The process of claim 1 wherein SDG in said SDG-containing extract is obtained in a yield of at least about 70%.

14. A process for preparing a secoisolariciresinol diglycoside (SDG) concentrate from de-fatted flaxseed comprising:
   (a) extracting de-fatted flaxseed with an extraction solvent comprising acetone and water at proportions ranging from about 35% acetone/65% water to about 65% acetone/35% water to obtain an SDG-containing extract;
   (b) separating residual solids from the SDG-containing extract;
   (c) removing acetone to provide an acetone stripped extract;
   (d) lowering the pH of the acetone stripped extract to precipitate SDG;
   (e) separating precipitated SDG from the acetone stripped extract;
   (f) subjecting the precipitated SDG in an aqueous slurry to hydrolysis to liberate free SDG; and
   (g) recovering the free SDG from the aqueous slurry.

15. The process of claim 14 wherein said recovering step comprises adjusting the pH of the aqueous slurry and removing water by lyophilization, spray drying, vacuum drying, or other evaporative means.

16. The process of claim 14 wherein said hydrolysis comprises adding calcium hydroxide to the aqueous slurry containing said precipitated SDG to provide an alkaline mixture having a pH of about 10 to about 13.

17. The process of claim 16 wherein:
   hydrolysis is carried out at an elevated temperature; then
   insolubles in the aqueous slurry are separated from the aqueous slurry by filtration or centrifugation at an elevated temperature; and
   phosphoric acid is added to the filtrate or centrate to lower the pH.

18. The process of claim 17 wherein said recovering step comprises removing water by lyophilization, spray drying, vacuum drying, or other evaporative means to provide an SDG concentrate in a yield of at least about 70%.

* * * * *

UNITED STATES PATENT AND TRADEMARK OFFICE
CERTIFICATE OF CORRECTION

PATENT NO. : 6,806,356 B2
DATED : October 19, 2004
INVENTOR(S) : Thomas A. Dobbins et al.

It is certified that error appears in the above-identified patent and that said Letters Patent is hereby corrected as shown below:

<u>Column 6,</u>
Line 53, change "de-fatter" to -- de-fatted --.
Lines 57 and 60, change "the of" to -- of the --.

Signed and Sealed this

First Day of February, 2005

JON W. DUDAS
*Director of the United States Patent and Trademark Office*